(12) United States Patent
Sakata et al.

(10) Patent No.: US 10,197,527 B2
(45) Date of Patent: Feb. 5, 2019

(54) SAMPLING UNIT AND BIOSENSOR

(71) Applicant: THE UNIVERSITY OF TOKYO, Tokyo (JP)

(72) Inventors: Toshiya Sakata, Tokyo (JP); Taira Kajisa, Tokyo (JP); Yuya Miyazawa, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 219 days.

(21) Appl. No.: 15/320,024

(22) PCT Filed: Mar. 24, 2015

(86) PCT No.: PCT/JP2015/058903
§ 371 (c)(1),
(2) Date: Dec. 19, 2016

(87) PCT Pub. No.: WO2015/198668
PCT Pub. Date: Dec. 30, 2015

(65) Prior Publication Data
US 2017/0122899 A1 May 4, 2017

(30) Foreign Application Priority Data
Jun. 23, 2014 (JP) ................................ 2014-127845

(51) Int. Cl.
*G01N 1/00* (2006.01)
*G01N 27/414* (2006.01)
*G01N 27/416* (2006.01)

(52) U.S. Cl.
CPC ....... *G01N 27/4145* (2013.01); *G01N 27/414* (2013.01); *G01N 27/416* (2013.01)

(58) Field of Classification Search
CPC ...................................................... G01N 1/00
See application file for complete search history.

(56) References Cited

U.S. PATENT DOCUMENTS

| 4,872,956 A | 10/1989 | Kotani et al. |
| 4,933,048 A | 6/1990 | Lauks |
| 6,214,185 B1 | 4/2001 | Offenbacher et al. |
| 6,554,982 B1 | 4/2003 | Shin et al. |

(Continued)

FOREIGN PATENT DOCUMENTS

| CN | 1357105 A | 7/2002 |
| CN | 1432130 A | 7/2003 |
| EP | 2518482 A1 | 10/2012 |

(Continued)

OTHER PUBLICATIONS

Office Action corresponding to Chinese Application No. 201580033551.0 dated May 29, 2018.

(Continued)

*Primary Examiner* — Jyoti Nagpaul
(74) *Attorney, Agent, or Firm* — Myers Bigel, P.A.

(57) ABSTRACT

A sampling unit having a first receiving part (16) and a second receiving part (18), which receive a sample solution and are disposed separately from each other, wherein the first receiving part (16) comprises an identification substance (22) that binds to a substance to be detected, and separates the substance to be detected from substances not to be detected in the sample solution, and the second receiving part (18) is connected with a reference electrode (21) via a salt bridge part (25).

11 Claims, 2 Drawing Sheets

(56) References Cited

U.S. PATENT DOCUMENTS

2014/0077315 A1    3/2014    Bischopink et al.

FOREIGN PATENT DOCUMENTS

| EP | 2570803 B1 | 3/2018 |
|----|------------|--------|
| JP | S63-148159 A | 6/1988 |
| JP | 2004-184155 A | 7/2004 |
| JP | 2010-107496 A | 5/2010 |
| JP | 5447716 B1 | 3/2014 |
| JP | 5599012 B1 | 10/2014 |
| WO | 01/73124 A3 | 10/2001 |
| WO | 2005/003774 A1 | 1/2005 |

OTHER PUBLICATIONS

International Search Report corresponding to International Application No. PCT/JP2015/058903 dated Jun. 16, 2015.
Written Opinion of the International Searching Authority corresponding to International Application No. PCT/JP2015/058903 dated Jun. 16, 2015.
Notification Concerning Transmittal of International Preliminary Report on Patentability corresponding to International Application No. PCT/JP2015/058903 dated Jan. 5, 2017.
Springsteen et al. "A detailed examination of boronic acid-diol complexation", Tetrahedron 58:5291-5300 (2002).
Extended European Search Report corresponding to European Application No. 15812759.7 dated Nov. 23, 2017.

[Figure 1]
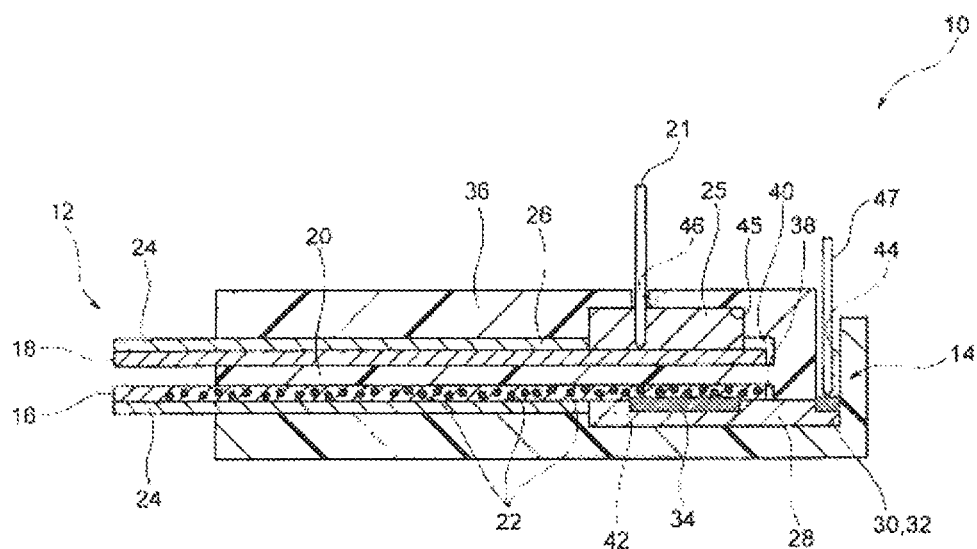
[Figure 2]
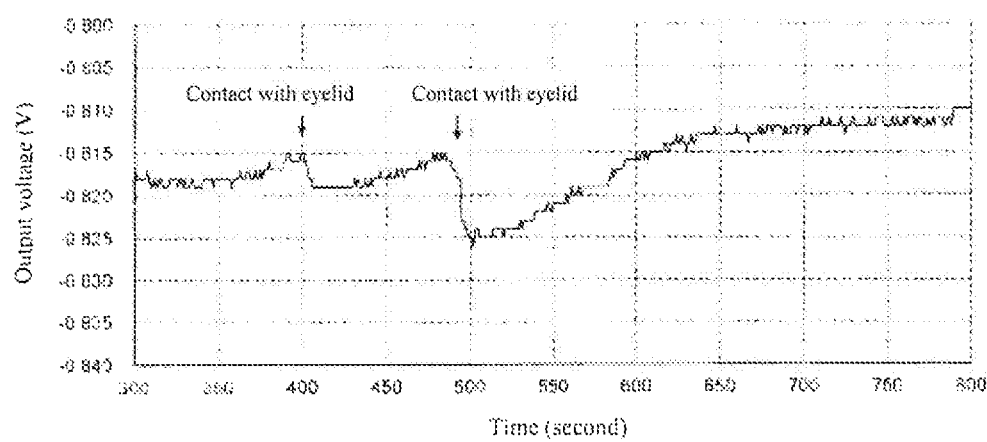

[Figure 3]
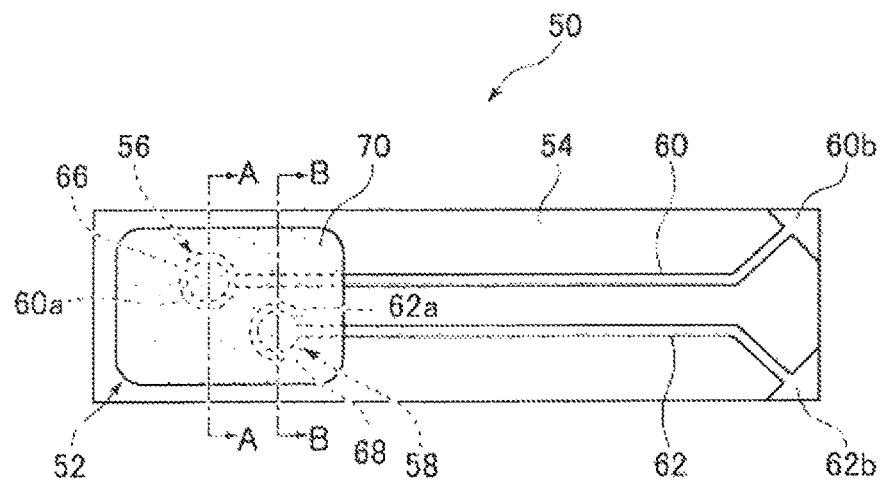
[Figure 4]
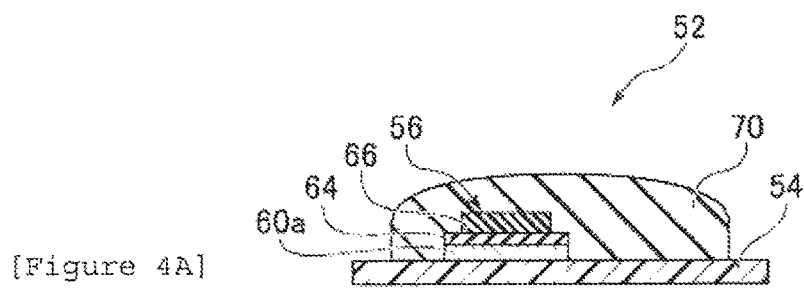
[Figure 4A]
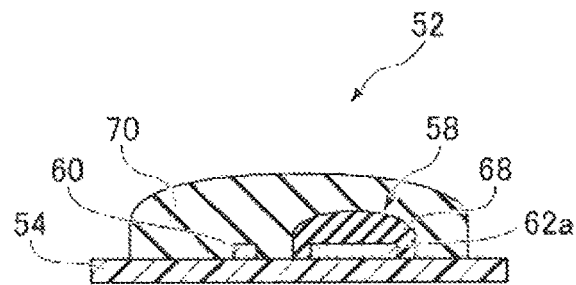
[Figure 4B]

SAMPLING UNIT AND BIOSENSOR

RELATED APPLICATIONS

This application is a 35 U.S.C. § 371 national phase application of PCT Application PCT/JP2015/058903 filed Mar. 24, 2015 which claims priority to Japanese Application No, 2014-127845 filed Jun. 23, 2014. The entire content of each is incorporated herein by reference in its entirety.

TECHNICAL FIELD

The present invention relates a sampling unit and a biosensor.

BACKGROUND ART

In recent years, as a biosensor, a technique capable of noninvasively utilizing living cells in analyses has been disclosed (for example, Patent Literature 1). Patent Literature 1 discloses a biosensor having a structure in which a detection surface for detecting a change in the physical properties of a negative charge is covered with a phenylboronic acid group binding to a sialic acid sample (cells themselves or a sugar chain derived from the cells).

CITATION LIST

Patent Literature

Patent Literature 1: Japanese Patent Laid-Open No. 2010-107496

SUMMARY OF INVENTION

Technical Problem

The aforementioned biosensor described in Patent Literature 1 is not invasive to cells or the like, but it cannot be said that this biosensor is not invasive to a human body when cells are collected therefrom. That is to say, it is desired to develop a biosensor capable of reducing a burden on a human body, for example, a biosensor capable of detecting a detection target based on tears, sweat, saliva, etc. It is to be noted that tears and the like contain not only glucose as a substance to be detected, but also contain proteins such as albumin, and thus, such tears are problematic in that the proteins contained therein would become noises and decrease measurement sensitivity.

Hence, it is an object of the present invention to provide a sampling unit and a biosensor, which are capable of making an analysis based on a sample noninvasively collected from a human body.

Solution to Problem

The sampling unit according to the present invention has a first receiving part and a second receiving part, which receive a sample solution and are disposed separately from each other, wherein the first receiving part comprises an identification substance that binds to a substance to be detected, and separates the substance to be detected from substances not to be detected in the sample solution, and the second receiving part is connected with a reference electrode via a salt bridge part.

The biosensor according to the present invention comprises the above described sampling unit and a field effect transistor in which the first receiving part is electrically connected with a gate electrode.

Advantageous Effects of Invention

According to the present invention, measurement sensitivity can be improved by suppressing the binding of a substance not to be detected to an identification substance contained in a first receiving part. Accordingly, the concentration of a substance to be detected can be more reliably measured based on a sample solution that has been noninvasively collected from a human body.

Moreover, by disposing a first receiving part and a second receiving part separately from each other, and by forming the receiving parts such that the collected sample solutions are not mixed with each other, a tear fluid can be electrically connected with a reference electrode via a salt bridge part, thereby achieving miniaturization.

BRIEF DESCRIPTION OF DRAWINGS

FIG. 1 is a longitudinal section view schematically showing the configuration of the biosensor according to a first embodiment.

FIG. 2 is a graph showing the results obtained by measuring the electrical properties of the biosensor according to the first embodiment.

FIG. 3 is a partial top view schematically showing the configuration of the biosensor according to a second embodiment.

FIG. 4 is a section view schematically showing the configuration of the biosensor according to the second embodiment. FIG. 4A is a section view made with the A-A line shown in FIG. 3, and FIG. 4B is a section view made with the B-B line shown in FIG. 3.

DESCRIPTION OF EMBODIMENTS

Hereinafter, the embodiments of the present invention will be described in detail, with reference to drawings.

First Embodiment (Entire Configuration)

A biosensor 10 shown in FIG. 1 comprises a sampling unit 12 and a field effect transistor (FET Field Effect Transistor) 14. The biosensor 10 identifies glucose as a substance to be detected contained in a sample solution in the sampling unit 12, and converts the identified information to electrical signals in the FET 14, so that it detects the amount of the glucose in the sample solution. Herein, the sample solution is a noninvasively collected sample solution, namely, biological solutions other than blood, such as sweat, tears, and saliva. These sample solutions do not only comprise glucose, but also comprise substances not to be detected that are proteins such as albumin.

The sampling unit 12 has two receiving parts that are disposed separately from each other, namely, a first receiving part 16 and a second receiving part 16. The first receiving part 16 and the second receiving part 18 are each formed, so that a sample solution can be moved from a tip thereof to a base end thereof, and the two receiving parts are separated from each other by a separation part 20. The separation part 20 can prevent the sample solutions each moving from the tip to the base end, from being mixed with each other.

While the first receiving part 16 allows a sample solution to move from the tip thereof to the base end thereof, it separates glucose from proteins contained in the sample solution. In the case of the present embodiment, the first receiving part 16 is formed with filter paper that has been cut into a rectangular shape.

The first receiving part 16 is electrically connected with the FET 14 on the base end side. The first receiving part 16 comprises an identification substance 22. The identification substance 22 has the function to bind to glucose contained in the sample solution. As such an identification substance 22, phenylboronic acid can be used, and other examples of the identification substance 22 include a derivative of phenylboronic acid (e.g., phenylboronic acid having a vinyl group, etc.), a glucose-binding protein (GBP), and a derivative thereof. For example, when phenylboronic acid binds to glucose, it generates a negative charge.

In the case of the present embodiment, the identification substance 22 is carried on a carrier (not shown in the figure). As such a carrier, conductive particles and nonconductive particles can be used. Examples of the conductive particles that can be used herein include metallic particles such as the particles of Au, Pt, Ag or Cu, non-metallic particles such as indium tin oxide (ITO), and the particles of conductive polymers. In addition, examples of the nonconductive particles that can be used herein include the particles of $SiO_2$. For instance, a thiol group (—SH) or a disulfide group (—S—S—) is introduced into the phenylboronic acid used as an identification substance 22 to form a thiol or disulfide derivative, so that the phenylboronic acid can be carried on the surface of an Au particle.

In the first receiving part 16, an elastic part 24 may be formed. In the case of the present figure, the elastic part 24 is formed on a surface opposite to the surface facing to the second receiving part 18. Moreover, the elastic part 24 is not formed on the base end side of the first receiving part 16. The elastic part 24 can be formed with a material having biocompatibility, such as hydrogel. The hydrogel is a gelatinous material with excellent water absorbency, which retains a large amount of water as a result of crosslinking among hydrophilic polymer chains. Examples of the hydrogel include agarose, silicone, polyhydroxyethyl methacrylate (Poly-HEMA, which is also referred to as 2-hydroxyethyl polymethacrylate), polyvinyl pyrrolidone (PVP), and polyvinyl alcohol (PVA). Poly-HEMA may be a homopolymer of hydroxyethyl methacrylate (HEMA), or it may also be a copolymer with another monomer (e.g., 2,3-dihydroxypropyl methacrylate, glycerol methacrylate (GMA), etc). It is to be noted that Poly-HEMA tends to have a higher water content percentage when it is in the form of a copolymer. Moreover, PVP may be a homopolymer of N-vinyl-2-pyrrolidone (NVP), or it may also be a copolymer formed by adding HEMA, methyl methacrylate (MMA), etc., and a crosslinker, to NVP as a main ingredient, and then polymerizing them.

The second receiving part 18 is not particularly limited, and for example, paper can be used as such a second receiving part 18. The paper is produced by agglutinating fibers such as plant fibers. The plant fibers are composed of cellulose or hemicellulose. Cellulose has the properties that a large number of hydroxyl groups contained therein bind to one another via hydrogen bonds, and thereby plant fibers constituting paper adhere to one another. Examples of other fibers include fibrous products made from mineral, metal, synthetic resin and other materials.

The second receiving part 18 is connected with a reference electrode 21 via a salt bridge part 25 on the base end side thereof. The salt bridge part 25 is formed, for example, by consolidating a potassium chloride aqueous solution with agar or the like. A sample solution moving through the second receiving part 18 is electrically connected with the reference electrode 21, without directly contacting with the reference electrode 21 due to the salt bridge part 25.

As in the case of the first receiving part 16, an elastic part 24 may be formed in the second receiving part 18. In the case of the present figure, the elastic part 24 is formed on a surface opposite to the surface facing to the first receiving part 16. The elastic part 24 is not formed on the base end side of the second receiving part 18, on which the salt bridge part 25 is established.

The FET 14 comprises a source electrode part 30 that is electrically connected with a source (not shown in the figure) formed on the surface of a semiconductor substrate 28, a drain electrode part 32 that is electrically connected with a drain not shown in the figure) formed thereon, and a gate insulator film (not shown in the figure) that is formed on the semiconductor substrate 28, the source electrode part 30, and the drain electrode part 32. Both n-MOS and p-MOS can be used for the FET 14. On the gate insulator film, a gate electrode 34 is formed. The gate electrode 34 can be formed with Au, Ag, Cu, or the like. The source electrode part 30 and the drain electrode part 32 are electrically connected with a power source and a measuring instrument, although they are not shown in the figure.

The semiconductor substrate 28 may be formed with Si, Ga, As, ITO, IGZO, IZO or the like. Alternatively, an organic semiconductor, a carbon semiconductor (e.g., a carbon nanotube, a graphene semiconductor, a diamond semiconductor, etc.), or the like can be used as such a semiconductor substrate 28. The gate insulator film can be formed with an oxide or a nitride, such as $SiO_2$, $Si_3N_4$ ($SiN_x$), $Ta_2O_5$ or $Al_2O_3$.

In the case of the present embodiment, the biosensor comprises a main body 36 that retains a sampling unit 12 and an FET 14. The main body 36 is a cubic member formed with a synthetic resin such as polyethylene terephthalate (PET) or polytetrafluoroethylene (PTFE), and has a first receiving part installation part 38, a second receiving part installation part 40, an FET installation part 42, a separation part 20, a probe insertion hole 44, and a reference electrode insertion hole 46.

In the main body 36, two holes each extending from one end to another end in the longitudinal direction are formed on the top and bottom of one surface in the thickness direction. The lower hole is a first receiving part installation part 38, and the upper hole is a second receiving part installation part 40. Between the first receiving part installation part 38 and the second receiving part installation part 40, a separation part 20 is formed.

On the side of the other end of the first receiving part installation part 38, an FET installation part 42 is formed. In the FET installation part 42, there is formed a probe insertion hole 44 that leads to the surface of the other end side in the longitudinal direction of the main body 36. With regard to the probe insertion hole 44, the two probe insertion holes are established in line in a direction vertical to the paper surface of the present figure.

On the side of the other end of the second receiving part installation part 40, a salt bridge installation part 45 is formed. In the salt bridge installation part 45, there is formed a reference electrode insertion hole 46 that leads to the surface of the other end side in the longitudinal direction of the main body 36.

In the FET installation part 42, the FET 14 is established in a state in which the source electrode part 30 and the drain electrode part 32 are each fit to the probe insertion holes 44. In the FET 14, the gate electrode 34 is disposed at a connection part with the first receiving part installation part 38. The first receiving part 16 is installed to the first receiving part installation part 38 in a state in which the elastic part 24 is disposed on the lower side. Moreover, a tip of the first receiving part 16 is projected from one end of the main body 36, and the surface on the base end side is contacted with the gate electrode 34 of the FET 14. Into each of the probe insertion holes 44, a probe electrode 47 is inserted. The tips of the probe electrode 47 are contacted with the source electrode part 30 and the drain electrode part 32, respectively, and they are electrically connected with a source and a drain, respectively.

The salt bridge installation part 45 is filled with the salt bridge part 25. The second receiving part 18 is installed to the second receiving part installation part 40 in a state in which the elastic part 24 is disposed on the upper side. Moreover, a tip of the second receiving part 18 is projected from one end of the main body 36, and the surface on the base end side is contacted with the salt bridge part 25. Into the reference electrode insertion hole 46, the reference electrode 21 is inserted. The tip of the reference electrode 21 is inserted into the salt bridge part 25, and thus is electrically connected with the salt bridge part 25. The reference electrode 21 serves as a reference potential in the FET 14.

(Action and Effects)

In the thus configured biosensor 10, first, a sample solution is collected in the sampling unit 12. For example, the tip of sampling unit 12 is allowed to directly come into contact with the inner side of a lower eyelid, so to collect a tear fluid used as a sample solution. In the case of the present embodiment, since the elastic parts 24 are established on the tip sides of the first receiving part 16 and the second receiving part 18, a tear fluid can be collected without damaging an eyeball or the peripheral skin.

The collected tear fluid permeates from a tip towards a base end, in each of the first receiving part 16 and the second receiving part 18. In the case of the present embodiment, the first receiving part 16 is formed with filter paper, so that glucose in the tear fluid permeates into the receiving part more quickly than proteins. The glucose binds to the identification substance 22 in the first receiving part 16. Thereby, the identification substance 22 generates a negative charge. On the other hand, in the second receiving part 18, the tear fluid permeates into the base end side and then reaches the salt bridge part 25, so that the tear fluid is electrically connected with the reference electrode 21 via the salt bridge part 25.

The above described negative charge gives charge to the surface of the gate electrode 34 on the base end side of the receiving part 16. Thereby, a charge density on the gate electrode 34 is changed. This change in the charge density can be calculated as a change in the drain current passing from the source to the drain, using the potential of the tear fluid on the reference electrode 21 as a reference. Practically, a change in the charge density on the gate electrode 34 is calculated change in the gate voltage.

In the case of the present embodiment, the first receiving part 16 is formed with filter paper, so that glucose in the tear fluid permeates into the receiving part more quickly than proteins, and as a result, the glucose reaches the base end side of the first receiving part 16 more quickly than proteins. Thereby, the biosensor 10 can suppresses the binding of such proteins to the identification substance 22 contained in the first receiving part 16, or adhesion of such proteins to the surface of the gate electrode 34, so that unnecessary negative charge given to the gate electrode 34 can be suppressed. Accordingly, since the biosensor 10 is able to improve measurement sensitivity additionally, the amount of glucose can be more reliably measured, based on a sample solution that has been noninvasively collected from a human body.

Moreover, the biosensor 10 is formed, such that the first receiving part 16 is separated from the second receiving part 18 by the separation part 20 on their base end side, and such that sample solutions permeating from the tips of the two receiving parts are not mixed with each other on the base end side. Furthermore, the salt bridge part 25 is established on the base end side of the second receiving part 18. Thereby, in the biosensor 10, the reference electrode 21 that is electrically connected with the tear fluid via the salt bridge part 25 is used as a reference, and a change in the charge density on the gate electrode 34 that is connected with the other end side of the first receiving part 16 can be measured.

Practically, the biosensor 10 according to the above described embodiment was produced, and the output voltage of the FET 14, when the sampling unit 12 was allowed to come into contact with the inner side of a lower eyelid, was then measured.

Paper (manufactured by ADVANTEC, product name: Qualitative Filter Paper No. 131) was used as a first receiving part 16. Phenylboronic acid was used as an identification substance 22, and a gold particle (particle diameter: 15 nm) was used as a carrier paper was immersed in a solution containing phenylboronic acid-carried gold particles (concentration: 1 nM) to produce a first receiving part 16.

As a second receiving part 18, paper (manufactured by ADVANTEC, product name: Qualitative Filter Paper No. 131) was used. As a salt bridge part 25, agarose gel containing potassium chloride (concentration: 3.3 M) was used. A Pt electrode was used as a reference electrode 21.

As a separation part 20, a platy member formed with PTFE, having a thickness of 300 μm, was used. As a gate electrode 34 of an FET 14, an Au electrode was used.

A sampling unit 12 of the thus produced biosensor 10 was allowed to come into contact with a human eyeball for 10 seconds, and a change in the charge density on the gate electrode 34 was measured as a change in the voltage between the drain and the source. The results are shown in FIG. 2. In the present figure, the longitudinal axis indicates output voltage (V), and the horizontal axis indicates time (second). From the present figure, it could be confirmed that the output voltage was changed almost at the same time as the contacting of the sampling unit 12 with an eye. From these results, it could be confirmed that, in the biosensor 10, glucose in a tear fluid collected in the sampling unit 12 binds to the identification substance 22 in the first receiving part 16, and that the thus generated change in the charge density on the gate electrode 34 can be measured.

(Modification Example)

The present invention is not limited to the above described embodiment, and can be appropriately modified within the scope of the gist of the present invention.

For example, in the case of the above described embodiment, a case where the first receiving part 16 is formed with filter paper was explained. However, the present invention is not limited to this embodiment, and the first receiving part 16 may also be formed with a structure, such as a non-woven fabric made of a synthetic resin or organic polymer, having a flow channel.

In the case of the above described embodiment, a case where the identification substance 22 is carried on a carrier was explained. However, the present invention is not limited to this embodiment, and self-assembled monolayers (SAMs) comprising the identification substance 22 and an inhibitory substance may also be formed. The inhibitory substance prevents a protein such as albumin that is a substance not to be detected from binding to phenylboronic acid or from reaching the gate electrode 34. The term "SAMs" is generally used to mean organic in films, in which organic molecules are spontaneously gathered to one another at the interface between a solid and a liquid, or at the interface between a solid and a gas, to spontaneously form monomolecular films. In this case, the inhibitory substance is formed with a high molecular weight compound. As such a high molecular weight compound, an oligoethylene glycol having a molecular chain longer than the identification substance can be used, and for example, polyethylene glycol can also be used.

Moreover, the first receiving part 16 may also be a copolymer formed by binding the identification substance 22 to an inhibitory substance. In this case, the inhibitory substance can be formed with a hydrophilic polymer. The hydrophilic polymer is a polymer having a hydrophilic functional group (a hydroxyl group or a carboxyl group), and examples of the hydrophilic polymer include hydrogel, paper, and a superabsorbent polymer (SAP).

The hydrogel is a gelatinous material with excellent water absorbency, which retains a large amount of water as a result of crosslinking among hydrophilic polymer chains. Examples of the hydrogel include polyhydroxyethyl methacrylate (Poly-HEMA, which is also referred to as 2-hydroxyethyl polymethacrylate), polyvinyl pyrrolidone (PVP), and polyvinyl alcohol (PVA). Poly-HEMA may be a homopolymer of hydroxyethyl methacrylate (HEMA), or it may also be a copolymer with another monomer (e.g., 2,3-dihydroxypropyl methacrylate, glycerol methacrylate (GMA), etc.). It is to be noted that Poly-HEMA tends to have a higher water content percentage when it is in the form of a copolymer. Moreover, PVP may be a homopolymer of N-vinyl-2-pyrrolidone (NVP), or it may also be a copolymer formed by adding HEMA, methyl methacrylate (MMA), etc., and a crosslinker, to NVP as a main and then polymerizing them.

The paper is produced by agglutinating fibers such as plant fibers. The plant fibers are composed of cellulose or hemicellulose. Cellulose has the properties that a large number of hydroxyl groups contained therein bind to one another via hydrogen bonds, and thereby plant fibers constituting paper adhere to one another. Examples of other fibers include fibrous products made from mineral, metal, synthetic resin and other materials. From the viewpoint of more strongly fixing the identification substance 22, paper formed with plant fibers (cellulose) is preferable.

SAP is a polymer capable of absorbing and retaining water that is hundreds to thousands times heavier than the weight thereof. As such SAP, an acrylic acid polymer can be used. Since such an acrylic acid polymer has a large number of carboxyl groups, it has high hydrophilicity, and further, when SAPs are crosslinked to a fine structure, so that they can be processed in the form of sodium salts, they become gel having high water absorbency.

Examples of other hydrophilic polymers include: cellulose derivatives such as hydroxypropylmethyl cellulose (HPMC), carboxymethyl cellulose sodium (CMC-Na), or hydroxyethyl cellulose (HEC); Polysaccharides such as alginic acid, hyaluronic acid, agarose, starch, dextran, or pullulan, and the derivatives thereof; homopolymers such as a carboxyvinyl polymer, polyethylene oxide, poly(meth)acrylamide or poly(meth)acrylic acid, copolymers of the homopolymers and polysaccharides, and copolymers of monomers constituting the aforementioned homopolymers and other monomers; proteins such as collagen or gelatin, and the derivatives thereof; and polysaccharides or mucopolysaccharides, such glycosaminoglycan selected from among heparin, hyaluronic acid, chondroitin sulfate, dermatan sulfate, dextran sulfate, keratan sulfate and heparan sulfate, chitin, and chitosan.

Furthermore, there may be used hydrophilic polymers, such as 1-vinyl-2-pyrrolidinone, propenoic acid 2-methyl ester, monomethacryloyloxyethyl phthalate, ammonium sulphatoethyl methacrylate, N-vinylpyrrolidone, N,N-dimethylacrylamide, or 2-(methacryloyloxyethyl)-2-(trimethylammonioethyl) phosphate.

The above-exemplified hydrophilic polymers may be used singly or in combinations of two or more.

As a polymerization initiator, a known radical polymerization promoter can be selected and used on a timely basis. Preferably, a radical polymerization promoter, which has water solubility or water dispersibility and is homogeneously contained in the entire system, is preferably used. Specifically, examples of the polymerization initiator include water-soluble peroxides such as potassium peroxodisulfate or ammonium peroxodisulfate, water-soluble azo compounds such as VA-044, V-50 or V-501 (all of which are manufactured by Wako Pure Chemical industries, Ltd.), and a mixture of $Fe^{2+}$ and hydrogen peroxide.

As a crosslinker, N,N'-methylenebisacrylamide, ethylene glycol dimethacrylate, vinyl methacrylate, or the like can be used.

In the above described embodiment, the first receiving part 16 has a structure in which the first receiving part entirely contains the identification substance 22 from the tip side to the base end side, but the structure is not limited thereto. It may be possible to adopt a structure, in which the identification substance 22 binding to glucose is contained in the base end side of the first receiving part 16, whereas in the tip side of the first receiving part 16, a substance to which substances other than glucose (e.g., proteins such as albumin) preferentially adhere, specifically, a substance easily binding to a thiol group, a gold particle, or a platinum particle is contained. By adopting such a structure, measurement sensitivity can be preferably increased.

Moreover, in the case of the above described embodiment, a case where the separation part 20 is formed integrally with the main body 36 was explained. However, the present invention is not limited to this embodiment, and the separation part 20 may also be formed independently and separately from the main body 36.

In the case of the above described embodiment, a case where the main body 36 retains the sampling unit 12 and the FET 14, so that it is configured integrally with the sampling unit 12 and the FET 14, was explained. However, the present invention is not limited to this embodiment, and the biosensor may be configured with a first main body 36 retaining the sampling unit 12 and a second main body 36 retaining the FET 14. Thereby, only the sampling unit can be exchanged with another one in the biosensor.

In the case of the above described embodiment, a case where the substance to be detected is glucose was explained. However, the present invention is not limited to this embodiment. For example, the present invention may be applied to a sodium ion or a potassium ion used as a substance to be detected. In this case, the identification substance can be crown ether.

In the case of the above described embodiment, a case where the reference electrode 21 is inserted into the salt bridge part 25 was explained. However, the present invention is not limited to this embodiment, and the reference electrode may also be formed on the salt bridge part 25 by directly forming a thin film on the salt bridge part.

In the case of the above described embodiment, a case where the second receiving part 18 is formed with paper was explained. However, the present invention is not limited to this embodiment, and the second receiving part may also be formed with hydrogel. In this case, the elastic part 24 is not necessarily established on the second receiving part 18.

Second Embodiment (Entire Configuration)

A biosensor 50, shown as a partial upper view in FIG. 3, comprises a measurement electrode 60 and a reference electrode 62, which are formed separately from each other on a substrate 54 having a rectangular shape. The measurement electrode 60 and the reference electrode 62 are formed along the long side of the substrate 54, and base ends 60b and 62b of both electrodes reach the ends of the substrate 54. A first receiving part 56 is established on the tip of the measurement electrode 60, and a second receiving part 58 is established on the tip of the reference electrode 62. The first receiving part 56 and the second receiving part 58 are disposed separately, and the first and second receiving parts 56 and 58 constitute a sampling unit 52, as described later. As in the case of the first embodiment, the biosensor 50 identifies glucose as a substance to be detected contained in a sample solution in the sampling unit 52, and converts the identified information to electrical signals in an FET that is not shown in the figure, so that it detects the amount of the glucose in the sample solution.

As such a substrate 54, for example, a glass can be used. The measurement electrode 60 can be formed, for example, from a gold electrode. The base end 60b side of to measurement electrode 60 is electrically connected with the FET that is not shown in the figure. In the present embodiment, the base end 60b side of the measurement electrode 60 can be used as a gate electrode of the FET. Since the measurement electrode 60 has the first receiving part 56 at the tip thereof, the gate electrode of the FET the biosensor 50 is connected with the first receiving part 56.

In the sampling unit 52, the first receiving part 56 and the second receiving part 58 are disposed separately from each other. The thus separately disposed first receiving part 56 and second receiving part 58 are covered with a porous elastic layer 70. The porous elastic layer 70 can be formed with a material having biocompatibility, for example, with porous gel prepared by making porous hydrogel. An example of such hydrogel is polyhydroxyethyl methacrylate, as described in the first embodiment.

As shown in FIG. 4A, the first receiving part 56 is prepared by establishing a MIP (molecular imprinted polymer) gel layer 66 on the surface of the tip 60a of the measurement electrode 60. The MIP gel layer 66 is a gel layer comprising an identification substance, and the gel layer is formed with hydrogel. As such an identification substance, a compound having the function to bind to glucose contained in a sample solution can be used, as in the case, of the first embodiment. Moreover, an example of the hydrogel is polyhydroxyethyl methacrylate, as described in the first embodiment.

In the MIP gel layer 66 of the first receiving part 56, glucose in the sample solution permeating through the porous layer 70 is separated from proteins.

In the first receiving part 56 shown in the figure, a blocking layer 64 is established between the tip 60a and the MIP gel layer 66 in the measurement electrode 60. The blocking layer 64 comprises an inhibitory substance. The inhibitory substance has an action to eliminate proteins, and for example, a monomolecular film of albumin can be used. As explained in the first embodiment, the inhibitory substance prevents proteins as substances not to be detected from reaching the gate electrode.

As shown in FIG. 4B, the second receiving part 58 has a configuration in which a conductor part 62a is covered with a salt bridge part 68. In the present embodiment, the conductor part 62a is formed integrally with the reference electrode 62, and the tip of the reference electrode 62 is used as such a conductor part 62a. The second receiving part 58 is connected with the reference electrode 62 via the salt bridge part 68. The reference electrode 62 can be formed, for example, by covering a gold electrode with silver/silver chloride. The gold electrode used herein can be the same as that of the measurement electrode 60. The salt bridge part 68 is preferably a gel layer that gives passage to water more hardly than in the case of the porous elastic layer 70. As with the first embodiment, the salt bridge part 68 is formed by consolidating a potassium chloride aqueous solution with agar or the like. When the sample solution permeates through the porous elastic layer 70 and reaches the second receiving part 58, the sample solution is electrically connected with the conductor part 62a as a tip of the reference electrode 62, without directly contacting with each other due to the salt bridge part 68, as in the case of the first embodiment. A base end 62b of the reference electrode 62, which is not shown in the figure, is connected with a measuring instrument.

The FET, which is not shown in the figure, basically has the same configuration as that of the first embodiment. As mentioned above, in the present embodiment, the base end 60b side of the measurement electrode 60 connected with the first receiving part 56 is used as a gate electrode of the FET. The reference electrode 62 connected with the second receiving part 58 serves as a reference potential in the FET.

(Action and Effects)

In the this configured biosensor 50, first, a sample solution is collected in the sampling unit 52. For example, the surface of the porous elastic layer 70 is allowed to directly come into contact with a lower eyelid, so as to collect a tear fluid used as a sample solution. In the case of the present embodiment, since the porous elastic layer 70 that covers the first receiving part 56 and the second receiving part 58 is established in the sampling unit 52, a tear fluid can be collected without damaging an eyeball or the peripheral skin.

The collected tear fluid permeates into the porous elastic layer 70 towards the first receiving part 56 and the second receiving part 58. In the case of the present embodiment, since the porous elastic layer 70 is formed with porous gel, glucose contained in the tear fluid permeates into the porous elastic layer 70 more quickly than proteins, and the glucose reaches the first receiving part 56. In the first receiving part 56, the glucose binds to an identification substance in the MIP gel layer 66. Thereby, the identification substance generates a negative charge. The proteins as substances not to be detected are blocked by the blocking layer 64. On the other hand, in the second receiving part 58, the tear fluid is electrically connected with the reference electrode 62 via the salt bridge part 68.

In the first receiving part 56, the identification substance is contained in the MIP gel layer 66. Since the glucose contained in the tear fluid is incorporated into a molecular template in the MIP gel layer 66, the effect of more reliably recognizing the glucose can also be obtained.

It is to be noted that the blocking layer 64 consisting of a monomolecular film of albumin does not have a precise structure having a flat surface. The monomolecular film of albumin has a structure in which the surface is complicated, and voids are present inside the film. The proteins as substances not to be detected are captured by such a complicated structure. In addition, into the voids in the monomolecular film, gel that forms the MIP gel layer 66 is incorporated, so that the MIP gel layer 66 is partially connected with the tip 60a of the measurement electrode 60. A negative charge generated in the MIP gel layer 66 moves through such gel and then can reach the tip 60a of the measurement electrode 60.

As in the case of the first embodiment, also in the second embodiment, the negative charge gives charge to the surface of the gate electrode. In the second embodiment, the above described negative charge moves from the first receiving part 56 through the measurement electrode 60 to the surface of the gate electrode that is on the base end 60b side of the measurement electrode 60, so as to give charge thereto. Thereby, a charge density on the gate electrode is changed. This change in the charge density can be calculated as a change in the drain current passing from the source to the drain, using the potential of the tear fluid on the reference electrode 62 as a reference. Practically, a change in the charge density on the gate electrode is calculated as a change in the gate voltage.

It the case of the present embodiment, since the porous elastic layer 70 is formed with porous gel, glucose contained in the tear fluid permeates into the porous elastic layer 70 more quickly than proteins, and the glucose reaches the first receiving part 56. In the first receiving part 56, the tear fluid permeates through the MIP gel layer 66 containing an identification substance into the blocking 64 containing an inhibitory substance. As described above, in the MIP gel layer 66, the glucose contained in the tear fluid binds to the identification substance, so that the identification substance generates a negative charge. Proteins as substances not to be detected are prevented from reaching the gate electrode by the inhibitory substance contained in the blocking layer 64.

Since adhesion of proteins to the surface of the gate electrode can be suppressed in the biosensor 50, unnecessary negative charge given to the gate electrode can be suppressed. Accordingly, since the biosensor is able to improve measurement sensitivity, the amount of glucose can be more reliably measured, based on a sample solution that has been noninvasively collected from a human body.

Moreover, in the biosensor 50, the first receiving part 56 and the second receiving part 58 are disposed separately from each other, and the porous elastic layer 70 consisting of porous gel is established such that it covers the first and second receiving parts 56 and 58. By the presence of the porous elastic layer 70, the tear fluid can permeate at a high speed and can reach the first receiving part 56 and the second receiving part 58 promptly.

As in the case of the first embodiment, by disposing the first receiving part 56 and the second receiving part separately from each other, a change in the charge density on the gate electrode that is on the side of the other end 60b of the measurement electrode 60 can be measured, using the reference electrode 62 that is electrically connected with the tear fluid as a reference.

Practically, the biosensor 50 according to the second embodiment was produced, and thereafter, the sampling unit 52 was allowed to come into contact with an eyeball and the movement was then confirmed.

Two gold electrodes were formed separately from each other on a substrate 54 consisting of glass according to a sputtering method. One gold electrode was used as a measurement electrode 60. The other gold electrode was covered with silver/silver chloride and was used as a reference electrode 62. The tip 60a of the measurement electrode 60 was subjected to a UV-ozone treatment, and was then immersed in a 5 g/L albumin solution overnight. After the resultant had been washed with water, it was dried to form a blocking layer 64 at the tip 60a of the measurement electrode 60.

Using, as a raw material, a monomer solution containing vinylphenylboronic acid (0.01 g) as an identification substance, an MIP gel layer 66 was formed on the blocking layer 64. Upon preparation of the monomer solution, 0.2 g of hydroxyethyl methacrylate (HEMA), 0.1 g of N-3-(dimethylamino)propyl methacrylamide, 0.02 g of N,N'-methylenebisacrylamide, 300 μL of 6.7 wt % sodium acrylate (pH 7.3), 0.009 g of glucose, and 0.01 g vinylphenylboronic acid were mixed with one another. To the obtained mixture, a 100 mM sodium phosphate buffer (pH 10.0) was added, so as to adjust the total amount to 1 g and dissolve the mixture in the buffer. Moreover, as polymerization initiators, 10 μL of a 50 mg/mL potassium peroxodisulfate solution (manufactured by Wako Pure Chemical Industries, Ltd.) and 2 μL of tetramethylenediamine (manufactured by Tokyo Chemical Industry, Co., Ltd.) were added to the resulting solution, so as to prepare a monomer solution used as a raw material for the MIP gel layer 66.

15 μL of the obtained monomer solution was added dropwise to the surface of the blocking layer 64 to form a coating film. This coating film was covered with a PET film, and thereafter, polymerization was carried out under a nitrogen atmosphere at a room temperature for 12 hours to produce hydrogel. After completion of the polymerization reaction, hydrogel was immersed in a 0.1 M hydrochloric acid/methanol solution overnight. Thereby, the remaining monomer components and glucose were removed, and an MIP gel layer 66 was formed. Thus, the blocking layer 64 and the MIP gel layer 66 were established on the surface of the tip 60a of the measurement electrode 60, thereby producing a first receiving part 56.

A silver/silver chloride ink (manufactured by BAS, product name: 011464 Silver Chloride Ink Used for reference electrode) was applied onto a gold electrode to be used as a reference electrode 62, and it was then dried in the air for 24 hours. After completion of the drying, a conductor part 62a, which was the tip of the measurement electrode 62 covered with silver/sliver chloride, was covered with agarose gel containing potassium chloride (concentration: 3.3 M) to form a salt bridge part 68, thereby obtaining a second receiving part 58. On the substrate 54, the first receiving part 56 and the second receiving part 58 were disposed separately from each other.

The first receiving part 56 and the second receiving part 58 were covered with the porous elastic layer 70 as follows, using a monomer solution. Herein, the monomer solution was prepared in the same manner as that for the raw material for the MIP gel layer, with the exception that vinylphenylboronic acid was not added as an identification substance. Then, 0.5 g of sodium chloride was added to the monomer solution to obtain at least a saturated aqueous solution, thereby preparing a raw material solution for the porous elastic layer 70.

The surface of the substrate 54 (the region other than the sampling unit 52), on which the first receiving part 56 and the second receiving part 58 were disposed separately from each other, was protected with hydrogel, and the back and side of the substrate 54 were also protected in the same manner as described above. The substrate 54, in which only the region of the sampling unit 52 was exposed, was immersed in the raw material solution for the porous elastic layer 70, and a polymerization reaction was then performed under a nitrogen atmosphere at a room temperature for 12 hours, so that hydrogel was produced on the substrate 54. After completion of the polymerization reaction, the substrate 54 was immersed in ultrapure water for 4 hours, so that the remaining monomer components and sodium chloride crystals were removed. Thus, the first receiving part 56 having the blocking layer 64 and the MIP gel layer 66, and the second receiving part 58 having the salt bridge part 68, were covered with the porous elastic layer 70, thereby forming the sampling unit 52.

The other end 60*b* of the measurement electrode 60 was used as a gate electrode of the FET to produce a biosensor 50. The sampling unit 52 of the obtained biosensor 50 was allowed to come into contact with a human eyeball, and a change in the charge density on the gate electrode was measured the same manner as in the case of the first embodiment. As a result, it could be confirmed that, in the biosensor 50, glucose contained in a tear fluid collected in the sampling unit 52 bound to an identification substance contained in the MIP gel layer 66, and that the thus generated change in the charge density on the gate electrode could be measured.

(Modification Example)

The present invention is not limited to the above described embodiment, and can be appropriately modified within the scope of the gist of the present invention.

For example, a separation part may be disposed on the substrate 54 between the first receiving part 56 and the second receiving part 58 in the sampling unit 52. The separation part can also be disposed between the measurement electrode 60 and the reference electrode 62. By establishing such a separation part, unintentional substances can be reliably prevented from reaching the reference electrode 62. The separation part can be formed, for example, by a means such as thermosetting using a hydrophobic material such as polydimethylpolysiloxane (PDMS) or epoxy.

The substrate 54 was formed with glass, but the material of the substrate is not limited thereto. As long as it is a flexible material having biocompatibility, for example, PDMS can be used as the substrate 54.

The first receiving part 56 was formed with a gold electrode. However, the material of the first receiving part is not limited thereto, and it may also be formed with silver, copper, platinum, palladium, mercury, etc. On the other hand, the second receiving part 58 cannot be only formed by covering a gold electrode with silver/silver chloride, but it can also be formed by covering an electrode consisting of, for example, silver or copper with silver/silver chloride.

As explained in the first embodiment, the raw material for the NIP gel layer 66 established on the surface of the first receiving part 56 can be prepared by arbitrarily combining a compound binding to glucose contained in a sample solution (an identification substance) with hydrogel, and then mixing a substance of interest (glucose) therewith. The raw material is prepared such that a desired molecular template can be obtained, and a commonly used means is then adopted, so as to form an MIP gel layer 66.

It is to be noted that, in the aforementioned embodiment, the gel layer containing an identification substance is an MIP gel layer containing a molecular imprinted polymer, but the gel layer is not necessarily limited thereto. In some cases, an identification substance is added to a gel layer that does not contain a molecular imprinted polymer, and the obtained mixture is established on the blocking layer 64, so as to configure a first receiving part 56.

The blocking layer 64 established between the MIP gel layer 66 and the first receiving part 56 may block proteins as substances not to be detected. Using any given inhibitory substance such as polyethylene glycol, as described in the first embodiment, the blocking layer 64 can be formed.

The salt bridge part 68 in the second receiving part 58 is not limited to agarose gel. As long as a layer, which is harder than the porous elastic layer 70 and through which a sample solution can permeate, can be obtained, the salt bridge part 68 can also be formed, for example, using HEMA.

The conductor part 62*a* in the second receiving part 58 can play its role, if it is electrically connected with the reference electrode 62. Thus, the conductor part 52*a* may not be always formed integrally with the reference electrode 62.

The porous elastic layer 70, which covers the first receiving part 56 and the second receiving part 58, can be hydrogel such as HEMA. A monomer solution is prepared using suitable salts that depend on the type of hydrogel, so that at least a saturated aqueous solution can be obtained, and the thus prepared monomer solution is used as a raw material for the porous elastic layer 70. When HEMA is used as hydrogel, for example, sodium chloride may be used as such salts.

As in the case of the first embodiment, the second embodiment can also be applied to a sodium ion or a potassium ion used as a substance to be detected. In this case, using crown ether as an identification substance, the MIP gel layer 66 can be produced by a prescription that depends on a desired substance to be detected.

REFERENCE SIGNS LIST

10 Biosensor
12 Sampling unit
16 First receiving part
18 Second receiving part
20 Separation part
21 Reference electrode
22 Identification substance
24 Elastic part
25 Salt bridge part
50 Biosensor
52 Sampling unit
54 Substrate
56 First receiving part
58 Second receiving part
60 Measurement electrode
62 Reference electrode
64 Blocking layer
66 MIP gel layer
68 Salt bridge part
70 Porous elastic layer

The invention claimed is:

1. A sampling unit having a first receiving part and a second receiving part, which receive a sample solution and are disposed separately from each other, wherein
the first receiving part comprises an identification substance that binds to a substance to be detected, and separates the substance to be detected from substances not to be detected in the sample solution, and the second receiving part is connected with a reference electrode via a salt bridge part.

2. The sampling unit according to claim 1, wherein a separation part is disposed between the first receiving part and the second receiving part, and the salt bridge part is established on the base end side of the second receiving part.

3. The sampling unit according to claim 2, wherein the sample solution permeates from a tip into a base end by capillary phenomenon, in the first receiving part and the second receiving part.

4. The sampling unit according to claim 2, wherein the first receiving part and the second receiving part have an elastic part on the tip side.

5. The sampling unit according to claim 2, wherein the identification substance is carried on a carrier.

6. The sampling unit according to claim 5, wherein the carrier is immobilized on the base end side of the first receiving part.

7. The sampling unit according to claim 1, wherein
the first receiving part and the second receiving part are disposed on a single substrate,
the first receiving part comprises a blocking layer comprising an inhibitory substance and a gel layer comprising an identification substance on the blocking layer, wherein the layers are successively laminated on the tip of a measurement electrode formed on the substrate, and
the second receiving part has a salt bridge part established on the tip of a reference electrode formed on the substrate.

8. The sampling unit according to claim 7, wherein the first receiving part and the second receiving part are covered with a porous elastic layer.

9. The sampling unit according to claim 7, wherein the gel layer comprises a molecular imprinted polymer.

10. The sampling unit according to claim 1, wherein the identification substance is phenylboronic acid.

11. A biosensor comprising
the sampling unit according to claim 1, and
a field effect transistor in which the first receiving part is electrically connected with a gate electrode.

* * * * *